United States Patent [19]
Kraft

[11] Patent Number: 5,660,841
[45] Date of Patent: Aug. 26, 1997

[54] PROCESS FOR PREPARATION OF AN INSECT-ACTIVE ASSEMBLY

[76] Inventor: Paul Kraft, 6 Imperial La., Spring Valley, N.Y. 10977

[21] Appl. No.: 636,031

[22] Filed: Apr. 22, 1996

[51] Int. Cl.$^6$ .................................................... A01N 25/34
[52] U.S. Cl. .......................... 424/403; 424/409; 424/411
[58] Field of Search .................................. 424/403, 411, 424/409

[56] References Cited

U.S. PATENT DOCUMENTS

| | | | |
|---|---|---|---|
| 3,857,934 | 12/1974 | Bernstein et al. | 424/30 |
| 3,864,468 | 2/1975 | Hyman et al. | 424/16 |
| 4,752,477 | 6/1988 | Kraft | 424/403 |

*Primary Examiner*—Thurman K. Page
*Assistant Examiner*—Kathryne E. Shelborne
*Attorney, Agent, or Firm*—Paul Kraft, Esq.

[57] ABSTRACT

An improved method is provided for preparing an insect-active assembly which can provide insect repellency, insecticidal action, or both and which is adapted to be directly affixed to the garment worn by a person. The assembly is comprised of a polymeric body which contains an insect-active composition, as a volatile plasticizer, which, over time, migrates from the polymeric body to provide the desired degree of insect-active action. The improvement consists of preparing the assembly at low temperatures thus preventing losses of the insect-active component to the environment, during processing under conditions employed in the prior art. A key element of this improved process is the use of a thermoplastic latex in place of thermoplastic resins or polymers used in earlier versions of assembly preparation. The thermoplastic latices, which have been plasticized with the insect-active composition, can readily be dried at low temperatures, to form the assembly.

16 Claims, No Drawings

PROCESS FOR PREPARATION OF AN INSECT-ACTIVE ASSEMBLY

BACKGROUND OF THE INVENTION

1. Field of Invention

The present invention relates to an improved method of manufacturing an insect-active assembly which can be attached to the garments of a person and which has "insect active" characteristic. The term insect active as used in the present specifications is intended to indicate that the article functions in regard to insect repellency, insecticidal action, or a combination of both, when placed in the intended environment on the garment of a person.

This invention specifically involves an improved process for preparing an insect-active assembly comprising a polymeric body which contains an insect-active composition, as a volatile plasticizer, which over time migrates from the polymeric body to provide the desired degree of insect-active action. The assembly can be affixed directly to the garment of a person by a variety of means including adhesive coatings and hook-and-loop fasteners. A major advantage of such an assembly is that it provides a degree of insect-activity without direct skin contact with the insect active agents; which may be physiologically harmful.

2. Description of Prior Art

U.S. Pat. No. 4,752,477, which is incorporated by reference, describes an assembly comprising a polymeric body which, contains an insect-active composition, which acts a volatile plasticizer. Over time the insect-active composition becomes fugitive and migrates from the polymeric body to provide the desired degree of insect-active action in the localized environment. The assembly can be affixed directly to the garment of a person by a variety of means including adhesive coatings and hook-and-loop fasteners. The major advantage of such an assembly is that it provides a degree of insect activity without direct skin contact with the insect active agents.

However the process by which this insect-active assembly is prepared, as demonstrated by the examples#1 & #2 of U.S. Pat. No. 4,752,477, exhibit certain manufacturing processes which could raise potential OSHA and environmental concerns. These concerns result from the high temperature blending of the insect-active composition with the polymeric body of the assembly. The technique described in examples #1 and #2 of U.S. Pat. No. 4,752,477, clearly demonstrate that very high temperatures (i.e. 300 degrees C.) are employed in order to attain the alloying, blending or intimate mixing of the two required components. However this high temperature blending process may result in the rapid loss of the expensive insect-active composition due to volatilization in the plant. As a direct consequence, problems of worker exposure to high levels of volatile fumes during high temperature processing may be expected. Such exposure could give rise to OSHA concerns. Additionally, the loss of such volatile and potentially toxic insect-active components to the atmosphere outside the plants parameter, could raise significant EPA concerns.

It became clear that an improved low temperature process was needed to avoid these high temperature processing problems; while still retaining the insect-active efficacy of the assembly. The instant invention represents such a significant improvement in the process for the preparation of the assembly described in U.S. Pat. No. 4,752,477.

SUMMARY OF THE INVENTION

An improved fabrication process, for the preparation of an insect-active assembly described in U.S. Pat. No. 4,752,477, has been developed which facilitates the incorporation of the insect-active composition into the polymeric body at significantly lower temperatures. These temperatures include, but not limited to room temperature i.e. 25 degrees centigrade). This is to be compared to the 200–300 degree centigrade range employed and described in U.S. Pat. No. 4,752,477. The key element of the improved process involves the specific use of thermoplastic latex to form the polymeric body. Typical of such latices are PVC, CPVC, ABS, styrene Acrilonitfile copolymers, butadiene acrylonitrile coplymers, acrylate and methacrylate polymers and coplymers, vinyl acetate acrylic polymers and coplymers, ethylene and propylene polymers and coplymers, and vinyl acetate olefins polymers and copolymers. Such latices typically exhibit minimum film forming temperatures at about room temperature to about 75 degrees centigrade. Such thermoplastic latices are subsequently plasticized with the insect-active composition described in U.S. Pat. No. 4,752,477 which act as a fugitive plasticizer.

As noted above, it has been observed that the components of various insect-active compositions, either alone or in combination, function as plasticizers for plasticizing the thermoplastic latices, in place of conventional plasticizers. Thus when these thermoplastic latices are plasticized with the insect-active compositions, they further suppress the minimum film forming temperatures of the resultant thermoplastic latex. On drying these plasticized thermoplastic latices, which have been plasticized with the insect-active composition, form uniform polymeric body which are flexible films or sheets. These films or sheets require no or minimal heating to be formed. The insect-active plasticizers contain therein are generally considered to be "secondary plasticizers"; which means that they are far more fugitive than primary plasticizers. As a result these plasticizers are readily released into the environment, as when attached to the garment. These resultant films or sheets can the be cut or shaped to meet the design of the specific garment configuration to which they are attached.

The volatile insect-active composition within the assembly acts as a fugitive plasticizer. Thus with the passage of time, the insect-active composition mimics the action of a fugitive plasticizer by defusing and volatilizing from the polymeric body to achieve the desired level of insect-active action in the immediate area in which the polymeric body is placed. The assembly is either configured so that it can be appropriately affixed per Se to a garment worn by a person (e.g. fashioned in the form of a head band to be placed around a person's hat) or it can have separate means to directly affix it to the garment worn by the person. The improvement over U.S. Pat. No. 4,752,477, consists of the low temperature method of manufacture of the insect-active assembly.

DETAILED DESCRIPTION OF THE PRESENT INVENTION

As noted above, this invention relates to an improved method of preparing an insect-active assembly described in U.S. Pat. No. 4,752,477, which is incorporated by reference un the present application. As described above, the assembly contains an insect-active composition which acts as a fugitive volatile plasticizer for the assembly. Since the plasticizer is volatile, it migrates from the polymer body to achieve the desired level of insect action (repellency, insecticidal action or both) in the environment in which the assembly is placed. This can for example be by directly affixed to a garment worn by a person. It is generally preferred to have the insect repellent composition since it acts to keep the insects away from the person wearing the assembly.

As observed in U.S. Pat. No. 4,752,477 the major portion of the assembly is a thermoplastic copolymer, such as for example polyvinylidene chloride-polyvinyl chloride, which can be appropriately fashioned in any desired shape or form. Suitable alternative thermoplastic polymer and copolymers include but not limited to, latices of PVC and it's copolymers, CPVC and it's copolymers, ABS, styrene Acrilonitrile copolymers, butadiene acrylonitrile coplymers, acrylate and methacrylate polymers and coplymers, vinyl acetate acrylic polymers and coplymers, ethylene and propylene polymers and coplymers, and vinyl acetate olefins polymers and copolymers. Such latices typically exhibit minimum film forming temperatures at about 15 degrees centigrade to about 100 degrees centigrade.

The insect-active components which are covered by the instant invention include those which can function as plasticizers for the thermoplastic latices. This includes such insect-active compositions which are capable of being emulsified with a surfactant and then mechanically blended into the thermoplastic polymer latex. In an other embodiment of this invention, the insect-active composition is directly dispersed into the latex without any addition of surfactants, by means of high speed agitation, stirring, shaking, mixing or a mechanical homogenizer.

Included as appropriate insect-active compositions suitable for this invention are the various ratios of blends of substituted and unsubstituted hexanediols, substituted toluamides, and synthetic or natural pyretherins, which are well recognized insect repellant materials. Two of such preferred insect-active compositions involve N,N'-diethyltohamide("DEET") and 2-Ethyl-1,3 Hexanediol in ratios that vary from 0% to 100% of each of the components. The mount of insect-active composition which can be added to the polymer body can vary and can preferability range from about 1 to 100 parts by weight of insect-active composition every 100 parts by weight of polymer. Factors such as time of day, season, humidity and temperature will determine to a large extent the type and level of insect-active component required.

In addition to those factors described in U.S. Pat. No. 4,752,477 for effecting the extent that a fugitive plasticizer/insect-active composition migrates from the polymer, in the instant improved process additional factors such as, the type and level of emulsifier present, if any, in the plasticized latex method. Surfactants will have an effect on migration rate of insect-active composition out of the assembly.

A preferred thermoplastic latices suitable for this invention are those that when plasticized with a suitable insect-active component, will exhibit low glass transition temperatures of about room temperature (i.e. about 25 degrees centigrade); thus forming continuous films or sheets upon drying. Typical of such preferred latices is GEON 652; Polyvinylidehe Chloride ($PVCl_2$)-Polyvinyl Chloride (PVC) copolymer sold by B. F. Goodrich GEON 450X20 add Vinyl Chloride-Acrylic Latex (from B. F. Goodrich). Additional latices that are suitable for this improved process include Vinyl Acetate/acrylic coplymers such as 76 RES-3077 from Union 76 Chemicals Company, acrylic copolymers such as 76 RES-6510 from Union 76 Chemicals Company as well as all acrylic polymer latices as well as polymer and copolymer latices of butadiene.

The foregoing is intended to supply a general description of the present invention with the Examples which follow being used to merely illustrate certain preferred embodiments thereof.

EXAMPLE 1

Emulsified Insect-Active Composition—as a Plasticizer for $PVCl_2$ Latex

Component A

A reaction vessel was charged with 15 grams of N,N'-diethyltoluamide("DEET") and 15 grams of pyretherin (Available as Premium PYROCYDE-175 from McLoughlin, Gormly, King & Company) were mixed with 1 gram "Triton X-45" surfactant from Rohm & Hass Company, which is a Octyl phenoxyethanol (5 oxyethylene units) to form Component A employing high speed stirring.

Component B

In a separate reaction vessel are charged 18 grams of deionized water is blended with 1½ grams of "TRITON X-100" sold by Rohm& Hass Company which is a Octyl phenoxyethanol (9–10 oxyethylene units) with agitation.

Components A and B are then blended together with high speed agitation using a "Lightning type" mixer for about 1–2 hours to form a stable emulsion of the insect-active composition.

EXAMPLE 2

The emulsified insect-active composition from Example 1 is then slowly (over a 5 minutes) added to 100 parts of a GEON 652 Polyvinylidene Chloride-Polyvinyl Chloride Latex (from B. F. Goodrich which contains 50 percent solids) employing high speed agitation. The resulting stable latex contains approximately 35 phr of insect-active composition per 100 parts of solids.

The resultant plasticized latex is then applied to a metal tray coated with TEFLON fluorocarbon polymer. Using a "Doctor Blade" draw down device to provide a uniform thickness, coating of 10 mils. The coating is then allowed to air dry at room temperature of about 25 degrees centigrade over a 10 hour period. This results in a continuous dried film or sheet containing the insect-active composition, acting as a plasticizer, within the coalesced Polyvinylidene Chloride-Polyvinyl Chloride film. The dried sheet of about 5 mils is removed from the TEFLON clad tray. The resultant plasticized sheet of Polyvinylidene chloride-Polyvinyl Chloride ($PVCl_2$-PVC) resin, containing the insect-active composition, was then coated with a pressure-sensitive adhesive and a release paper covering. The strips were easily bonded to garments by removal of the release paper and by then pressing and thereby attaching the flexible film of polyvinyl chloride to the garment by means of the pressure-sensitive adhesive coating.

EXAMPLE 3

This Example is the same as Example 2 except that the assembly of polyvinylidene chloride-Polyvinyl Chloride resin, which was plasticized with the insect repellent composition, coated with a pressure sensitive adhesive. However, instead of release paper covering, the assembly is bonded to a VELCRO hook-and loop fastener. The resultant assembly is then adapted for use on garments.

EXAMPLE 4

The emulsified insect-active composition from Example 1 is then slowly added to 100 parts of a GEON 459X20 Vinyl Chloride-Acrylic Latex (from B. F. Goodrich which contains 55 percent solids) with high speed agitation over a 5 minute period. The resulting latex contains approximately 33 phr of insect-active components per 100 parts of solids. This latex is then applied to a metal tray coated with TEFLON fluorocarbon polymer. Using a "Doctor Blade" device a uniform thickness coating of 5 mils is prepared. The resultant coating is then allowed to air dry at room temperature of about 25 degrees centigrade over a 5 hour period. This results in a continuous film of insect-active component acting as a plasticizer within the coalesced Vinyl Chloride-Acrylic Latex. The dried sheet of about 2.5 mils is removed from the metal tray clad with TEFLON fluorocarbon polymer. The resultant sheet of Vinyl Chloride-Acrylic resin, which was plasticized with the insect repellent composition, was then coated with a pressure-sensitive adhesive and a release paper covering. The strips were easily bonded to garments by removal of the release paper and by then pressing and thereby attaching the flexible film of Vinyl Chloride-Acrylic resin to the garment by means of the pressure-sensitive adhesive coating.

EXAMPLE 5

The emulsified insect-active components from Example 1 is then slowly added to 100 parts of an Acrylic Latex ("HYCAR 2600X288" from B. F. Goodrich which contains 50 percent solids) with high speed agitation over a 5 minute period. The resulting latex contains approximately 35 phr of insect-active composition per 100 parts of solids. This latex is then applied to a metal tray coated with TEFLON fluorocarbon polymer. Using a "Doctor Blade" device to provide a uniform thickness a coating of 5 mils is prepared. The resultant coating is then allowed to air dry at a temperature of about 40 degrees centigrade over a 3 hour period. This results in a continuous film of insect-active composition acting as a plasticizer within the coalesced Acrylic Latex. The dried assembly sheet of about 2.5 mils is removed from the metal tray clad with TEFLON fluorocarbon polymer. The resultant assembly sheet of Acrylic polymer, which was plasticized with the insect repellent composition, was then coated with a pressure-sensitive adhesive and a release paper covering. The strips were easily bonded to garments by removal of the release paper and by then pressing and thereby attaching the flexible Acrylic film to the garment by means of the pressure-sensitive adhesive coating.

EXAMPLE 6

A 4 inch×8 inch strip of assembly prepare by means of the process described in Example 2 is attached to the shirt sleeve of the user by first removing the release paper and then wrapping the assembly around the shirt sleeve. The user then employs the arm containing the assembly to support a fishing pole while fishing for 20 minutes over a flying insect infested stream when the temperature is 90 degrees Fahrenheit and the humidity is 60 percent. The effect of the insect-active composition was then observed. The results were then compared with varying levels of insect-active compositions and the results noted in the table below.

TABLE

EFFECT OF ASSEMBLY INSECT - ACTIVE CONTENT ON EFFICACY

| | Latex Percent *IAC | *IAC on phr | Effect on Insect Attack. |
|---|---|---|---|
| A | 50% DEET/%50 pyretherin | 35 phr | 1 insect landing on Hand |
| A | 100% DEET | 35 phr | 3 insect landing on Hand |
| A | 50% DEET/50% pyretherin | 10 phr | 5 insect landing on Hand |

TABLE-continued

EFFECT OF ASSEMBLY INSECT - ACTIVE CONTENT ON EFFICACY

| | Latex Percent *IAC | *IAC on phr | Effect on Insect Attack. |
|---|---|---|---|
| A | **Control - Dioctyl Phthalate | 35 phr | 10 insect landing on Hand |

*Insect-Active Components = IAC
**Control - Conventional Plasticizer with no-insect activity
A = GEON 652, a Polyvinlidene Chloride-Polyvinyl Chloride latex supplied by B.F. Goodrich Corporation.

The results clearly show that there is only one insect landing on the bare hand directly adjacent to the assembly that contained a 50 phr level (blend of DEET and pyretherin) of insect-active composition in the assembly affixed to the wrist. The results further show only 5 landings on the hand adjacent to the assembly that had a 35 phr level of insect-active composition in the assembly affixed to the wrist. This is in sharp contrast with the control assembly, where the insect active composition were replaced with a conventional commercial plasticizer control having no insect-active composition therein. This clearly demonstrates the effectiveness of an assembly prepared by the improved process of the instant invention.

I claim:

1. An improved process for the preparation of an insect-active assembly which comprises a polymeric body which contains a volatile insect-active composition as a volatile plasticizer therein, said polymeric body being adapted to be directly affixed to a garment worn by a person, wherein the improved process comprises:

(a) preparing said assembly from said polymeric body derived from a thermoplastic latex, (b) blending said insect-active composition into said thermoplastic latex, by means of agitation or as an aqueous emulsion or suspension, as a plasticizer therein, (c) casting a uniform 0.30 to 50 mil thickness coating of said thermoplastic latex, which contains said insect-active composition therein, on a non-stick release type surface, (d) allowing said plasticized thermoplastic latex coating, which contains said insect-active composition therein, to coalesce and dry into a film or sheet assembly at temperatures that range between 15 and 100 degrees centigrade; to form said polymeric body, (e) shaping said polymeric body, which contains the insect-active plasticizer composition therein, into said assembly configuration that can be affixed to garments worn by a person.

2. The process of claim 1 wherein said assembly is configured so that it is adapted to be directly affixed to the garment without separate attachment means.

3. The process of claim 1 wherein said assembly has a separate means attached to the polymeric body which is intended to be directly affix to a garment worn by a person.

4. The process of claim 3 wherein the means to affix the polymeric body to a garment comprises an adhesive coating on the polymeric body.

5. The process of claim 3 wherein the means to directly affix the polymeric body to a garment comprises components of a hook-and-loop fastener.

6. The process as claimed in claim 1 wherein the polymeric body is formed from a thermoplastic polymer or copolymer latices selected from the group consisting of, PVC and it's copolymers, CPVC and it's copolymers, ABS, styrene acrilonitrile copolymers, butadiene acrylonitrile coplymers, acrylate and methacrylate polymers and coplymers, vinyl acetate acrylic polymers and coplymers, ethylene and propylene polymers and coplymers, and vinyl acetate olefins polymers and copolymers.

7. The process of claim 1 wherein the thermoplastic polymer latex is a vinyl chloride-vinylidene chloride copolymer latex.

8. The process of claim 1 wherein the thermoplastic polymer latex is a vinyl chloride-acrylic copolymer latex.

9. The process of claim 1 wherein the thickness of said polymeric body containing the insect-active composition therein, upon drying, varies from 0.20 mils to 30 mils.

10. The process of claim 1 wherein the level of said insect-active composition in said polymeric body varies from 1 phr to 100 phr.

11. The process of claim 1 wherein the level of said insect active plasticizer composition in the polymeric body varies from 15 phr to 50 phr.

12. The process of claim 1 wherein said insect-active composition in the polymeric body is composed of N,N'-diethyltoluamide ("DEET") used alone or in combinations with naturally occurring or synthetic pyretherins or in combination with 2-Ethyl-1,3 Hexanediol; which are efficacious in repelling or killing various species of, ticks, mosquitoes, flys, bees, hornets, yellow jackets, wasps and biting, stinging or blood sucking insects.

13. The process of claim 1 wherein said insect-active composition in the polymeric body is a naturally occurring and or synthetic pyretherins.

14. The process of claim 1 wherein the insect-active composition in said polymeric body is composed of blends of 0.5% to 99.5% of N,N'-diethyltoluamide ("DEET") and 99.5% to 0.5% of naturally occurring or synthetic pyretherins and the level of said insect-active composition in said polymeric body varies from 1 phr to 100 phr.

15. The process of claim 1 wherein the insect-active composition in said polymeric body is composed of blends of 50% of N,N'-diethyltoluamide ("DEET") and 50% of naturally occurring or synthetic pyretherins and the level of said insect-active composition in said polymeric body 50 phr.

16. An insect-active assembly which comprises a polymeric body containing a volatile insect-active composition as a volatile plasticizer therein, said polymeric body being derived from a thermoplastic latex which has been plasticized with said insect-active composition, which upon drying yields said assembly; which can be adapted to be directly affixed to a garment worn by a person.

* * * * *